(12) United States Patent
Largeau et al.

(10) Patent No.: US 6,875,893 B2
(45) Date of Patent: Apr. 5, 2005

(54) PREPARATIONS OF A SULFINYL ACETAMIDE

(75) Inventors: Denis Largeau, Irigny (FR); Gilles Oddon, Genas (FR)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 10/443,327

(22) Filed: May 22, 2003

(65) Prior Publication Data

US 2004/0002547 A1 Jan. 1, 2004

Related U.S. Application Data

(60) Provisional application No. 60/383,173, filed on May 23, 2002.

(51) Int. Cl.⁷ ............................................. C07C 233/05
(52) U.S. Cl. ........................ 564/162; 514/618; 514/649
(58) Field of Search .......................... 564/162; 514/618, 514/649

(56) References Cited

U.S. PATENT DOCUMENTS

| | | | |
|---|---|---|---|
| 4,066,686 A | 1/1978 | Lafon | |
| 4,177,290 A | * 12/1979 | Lafon | 514/618 |
| 4,927,855 A | 5/1990 | Lafon | |
| 6,649,796 B2 | * 11/2003 | Naddaka et al. | 564/162 |
| 2002/0183552 A1 | 12/2002 | Naddaka | |

FOREIGN PATENT DOCUMENTS

EP      1 260 501      11/2002
WO   WO 02/10125      2/2002

OTHER PUBLICATIONS

D'Ouville et al., J. Am. Chem. Soc., vol. 60, 1938 pp. 33–36.
"Beilsteins Handbuch Der Organischen Chemie, 1$^{st}$ Supplement, vol. 5", 1930, Julius Springer, Berlin, DE, p. 279 (w/translation).
Skinner et al., J. Am. Chem. Soc., vol. 76, 1954, pp. 2776–2780.
Miyawaki et al, Heterocycles, vol. 54, No. 2, pp. 887–900, 2001.*

* cited by examiner

*Primary Examiner*—Shailendra Kumar
(74) *Attorney, Agent, or Firm*—Robert T. Hrubiec; Scott K. Larsen

(57) ABSTRACT

The present invention provides processes for the preparation of modafinil which includes the step of reacting benzhydrylthiol and chloroacetamide.

27 Claims, No Drawings

PREPARATIONS OF A SULFINYL ACETAMIDE

This application claims benefit of Provisional 60/383,173 filed May, 23, 2002.

The present invention is related to processes for the preparation of modafinil from benzhydrol and chloroacetamide.

FIELD OF THE INVENTION

The present invention is related to processes for the preparation of modafinil from benzhydrol and chloroacetamide.

BACKGROUND OF THE INVENTION

Modafinil, $C_{15}H_{15}NO_2S$, also known as 2-(benzhydrylsulfinyl) acetamide, or 2-[(diphenylmethyl) sulfinyl] acetamide, is a synthetic acetamide derivative with wake-promoting activity, the structure and synthesis of which has been described in French Patent No. 78 05 510 and in U.S. Pat. No. 4,177,290. Modafinil has been approved by the United States Food and Drug Administration for use in the treatment of excessive daytime sleepiness associated with narcolepsy, and is marketed under the name Provigil®. Provigil® is a pharmaceutical product comprising tablets containing 100 mg or 200 mg of modafinil.

The current invention provides an efficient process that allows for commercial manufacture of modafinil. The present invention discloses a process in which benzhydrylthiol is reacted with chloroacetamide to obtain the corresponding benzhydrylthioacetamide.

A synthesis of modafinil has been described in U.S. Pat. No. 4,177,290, where benzhydrol was reacted with chloroacetic acid.

A related process for synthesizing the levorotatory isomer of modafinil is disclosed in U.S. Pat. No. 4,927,855, issued May 22, 1990.

Processes for synthesizing modafinil derivatives are disclosed in U.S. Pat. No. 4,066,686, issued Jan. 3, 1978; U.S. Pat. No. 4,489,095, issued Dec. 18, 1984; U.S. Pat. No. 5,719,168, issued Feb. 17, 1998; PCT Publication No. 01/15752; and U.S. patent application Ser. No. 10/014,645.

Processes describing reaction of benzhydryl halides with 2-mercaptoacetates were described in U.S. Pat. No. 5,571,825; 4,964,893; EP Pat. No. 0,528 172; and *Chinese Journal of Medicinal Chemistry*,1999, 9, 132 .

Processes for preparing modafinil have been described in PCT Publication No. 02/10125.

The present invention provides an efficient process for the preparation of modafinil, which offers significant commercial advantages when preparing modafinil on an industrial scale. The current invention produces modafinil with fewer steps and at enhanced yields. Use of the chloroacetamide in the second step of the instant invention directly adds the desired amide group to the final product in one step. A further advantage of the instant processes is that the four reaction steps can be conducted in one reaction vessel, without isolation of the intermediates. This reduction in steps and the efficiency of the reaction steps also result in enhanced yields. An additional benefit of the present processes is a reduction in the undesirable waste products.

The current processes further provide for significant efficiencies in the commercial manufacture of modafinil. The overall costs and hazards of the manufacturing process are reduced, as simpler machinery can be used, less labor is involved and fewer undesirable waste products are generated, all of which provides distinct commercial advantages for the preparation of modafinil on a commercial scale.

SUMMARY OF THE INVENTION

The present invention is directed to processes for the preparation of modafinil, which is useful in the treatment of narcolepsy, among other disorders. One embodiment of the present invention is the reaction of benzhydrylthiol with chloroacetamide to obtain the corresponding benzhydrylthioacetamide.

DETAILED DESCRIPTION OF THE INVENTION

In one embodiment, the present invention provides a process of preparing modafinil comprising the step of reacting chloroacetamide with benzhydrylthiol to form 2-(benzhydrylthiol) acetamide. In a further aspect of the invention, the benzhydrylthiol is formed by reacting benzhydrol with thiourea and a suitable acid to form a S-benzhydrylthiouronium salt, followed by reacting the S-benzhydrylthiouronium salt with a suitable base. The reaction steps may conducted separately, where each intermediate is independently isolated, or the reaction steps are conducted in the same reaction vessel without isolation of any intermediates. A suitable acid can be hydrobromic acid, hydrochloric or sulfuric acid. A suitable base can be a metal hydroxide, and in particular, the metal hydroxide can be sodium hydroxide or potassium hydroxide. Any or all of the reaction steps can be conducted in a solvent system comprising water and an organic solvent selected from tetrahydrofuran, 1,2 -dimethoxyethane, MTBE, acetonitrile, chlorobenzene, ortho-dichlorobenzene, or methylcyclohexane. The temperature can range from about 25° C. to the refluxing temperature of the solvent system, and in particular, the temperature is from about 25–75° C.

In a further embodiment, the present invention provides a process of preparing modafinil comprising the steps of reacting chloroacetamide with benzhydrylthiol to form 2-(benzhydrylthiol) acetamide, and oxidizing 2-(benzhydrylthiol) acetamide.

In an additional embodiment, the present invention provides a process of preparing modafinil, comprising:

(1) reacting benzhydrol with a suitable acid and thiourea to form a S-benzhydrylthiouronium salt;

(2) reacting the S-benzhydrylthiouronium salt with a suitable base to form benzhydrylthiol;

(3) reacting the benzhydrylthiol with chloroacetamide to form 2-(benzhydrylthiol) acetamide;

(4) oxidizing 2-(benzhydrylthiol) acetamide with a suitable oxidizing agent to form modafinil.

In certain aspects, the suitable acid is selected from either hydrobromic or hydrochloric acid; and the suitable base is selected from potassium hydroxide or sodium hydroxide; and the process steps are conducted using either a water/tetrahydrofuran or a water/chlorobenzene solvent system. In other aspects, the process comprises the steps of:

(1) adding an aqueous 48% hydrobromic acid solution (about 1–10 equivalents) to benzhydrol and thiourea (about 1–10 equivalents) at a temperature of about 25–75° C., to form S-benzhydrylthiouronium salt;

(2) adding an aqueous solution of potassium hydroxide (about 1–10 equivalents), at a temperature of about 25–75° C., to the S-benzhydrylthiouronium salt to form the benzhydrylthiol;

(3) combining chloroacetamide as either a powder, or in solution with either water or a water/tetrahydrofuran mixture (about 1–10 equivalents) with the benzhydrylthiol at a temperature of about 25–75° C. to form 2-(benzhydrylthiol) acetamide.

In an additional aspect, the temperature for steps 1, 2, and 3 is from about 50–75° C. In other aspects, the 2-(benzhydrylthiol) acetamide is oxidized with a suitable oxidizing agent selected from m-chloroperoxybenzoic acid, sodium periodate, or hydrogen peroxide wherein the hydrogen peroxide may optionally be combined with an acid selected from hydrochloric or acetic acid. In further aspects, a 30% solution of hydrogen peroxide (about 1–2 equivalents) is combined with 2-(benzhydrylthiol) acetamide and acetic acid at a temperature of about 25–75° C. to form modafinil. The reaction steps may conducted separately, where each intermediate is independently isolated, or the reaction steps are conducted in the same reaction vessel without isolation of any intermediates.

In another embodiment, the present invention provides for a process of preparing modafinil comprising:
  (1) reacting benzhydrol, thiourea (about 1–3 equivalents) and an aqueous 48% HBr solution (about 1–3 equivalents) in aqueous tetrahydrofuran at about 70° C. to form S-benzhydrylthiouronium salt;
  (2) reacting the S-benzhydrylthiouronium salt with an aqueous potassium hydroxide solution (about 2–5 equivalents) at about 70° C. to form benzhydrylthiol;
  (3) reacting chloroacetamide (about 1.05–2 equivalents) in an aqueous tetrahydrofuran solution, with the benzhydrylthiol at about 70° C., to form 2-(benzhydrylthiol) acetamide;
  (4) reacting the 2-(benzhydrylthiol) acetamide with acetic acid (about 2–5 equivalents) and a 30% aqueous hydrogen peroxide solution (about 1.2–2 equivalents) to form modafinil.

In yet another embodiment, the present invention provides for a process of preparing modafinil comprising:
  (1) reacting benzhydrol, thiourea (about 1–3 equivalents) and an aqueous 48% HBr solution (about 1–3 equivalents) in aqueous chlorobenzene at about 70° C. to form S-benzhydrylthiouronium salt;
  (2) reacting the S-benzhydrylthiouronium salt with an aqueous potassium hydroxide solution (about 2–5 equivalents) at about 70° C. to form benzhydrylthiol;
  (3) reacting chloroacetamide (about 1.05–2 equivalents) in powder form with the benzhydrylthiol at about 70° C., to form 2-(benzhydrylthiol) acetamide;
  (4) reacting the 2-(benzhydrylthiol) acetamide with acetic acid (about 2–5 equivalents) and a 30% aqueous hydrogen peroxide solution (about 1.2–2 equivalents) to form modafinil.

As used herein, the term "about" refers to a range of values from ±10% of a specified value. For example, the phrase "about 50" includes ±10% of 50, or from 45 to 55.

The reactions of the synthetic methods claimed herein are carried out in suitable solvents which may be readily selected by one skilled in the art of organic synthesis, the suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular reaction or work-up following the reaction may be selected. Such suitable solvents, as used herein may include, by way of example and without limitation, chlorinated solvents, aromatic solvents, hydrocarbon solvents, ether solvents, polar protic solvents and polar aprotic solvents.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene.

Suitable aromatic solvents include, but are not limited to, benzene, toluene, ethylbenzene, xylene, chlorobenzene, dichlorobenzene, trichlorobenzene, nitrobenzene, benzonitrile, anisole, or pyridine.

Suitable hydrocarbon solvents include, but are not limited to cyclohexane, pentane, hexane, cycloheptane, methylcyclohexane, heptane, octane, indane, nonane, and can include the appropriate aromatic solvents, such as benzene, toluene, ethylbenzene, m-, o-, or p-xylene, etc.

Suitable ether solvents include, but are not limited to diethyl ether, t-butyl methyl ether ("MTBE"), 1,2-dimethoxyethane, 1,3-dioxane, 1,4-dioxane, furan, tetrahydrofuran ("THF"), or anisole.

Suitable polar protic solvents include, but are not limited to methanol, ethanol, propanol, butanol, butanol, i-butyl alcohol, t-butyl alcohol, methoxyethanol, ethoxyethanol, pentanol, neo-pentyl alcohol, t-pentyl alcohol, cyclohexanol, ethylene glycol, propylene glycol, benzyl alcohol, phenol, and glycerol.

Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, or hexamethylphosphoramide.

Suitable acids include, but are not limited to mineral acids such as hydrochloric acid, hydrobromic acid, sulfuric acid, nitric acid, phosphoric acid and perchloric acid; organic acids such as formic acid, acetic acid, trifluoroacetic acid, ethanolic acid, propionic acid, methane sulfonic acid, p-toluene sulfonic acid, benzene sulfonic acid, and caproic acid; or Lewis acids, such as boron trifluoride, aluminum chloride, stannic chloride, etc.

Suitable bases include, but are not limited to, inorganic bases such as sodium, lithium, and potassium salts of carbonates; sodium, lithium, and potassium salts of bicarbonates; sodium, lithium and potassium hydroxides and alkoxides, including tertiary alkoxides, such as tert-butoxide; barium, calcium and magnesium hydroxides; ammonium hydroxide; and organic nitrogen bases, such as tetrabutyl ammonium hydroxide, pyridine, piperidine, piperazine, morpholine, as well as organic amines such as methyl amine, dimethyl amine, ethyl amine, diethyl amine, triethyl amine, diisopropyl amine, butyl amine, aniline, benzyl amine, etc.

Suitable oxidizing agents include hydrogen peroxide, m-chloroperoxybenzoic acid ("m-CPBA"), $NaIO_4$, t-BuOCl, $Ca(OCl)_2$, $NaClO_2$, NaOCl, $HNO_3$, $K_2S_2O_8$, $O_2$, acylnitrates, sodium perborate, alkyl- and acyl peroxides, such as benzoyl peroxide; and hydroperoxides, such as t-butylhydroperoxide.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The present invention may be further understood by reference to Scheme 1, which provides a synthesis for modafinil. The scheme is meant to be illustrative of the present invention, and is not to be taken as limiting thereof. The synthesis, isolation and purification of modafinil can be accomplished by methods well known to the skilled artisan of organic synthesis, and by methods taught herein.

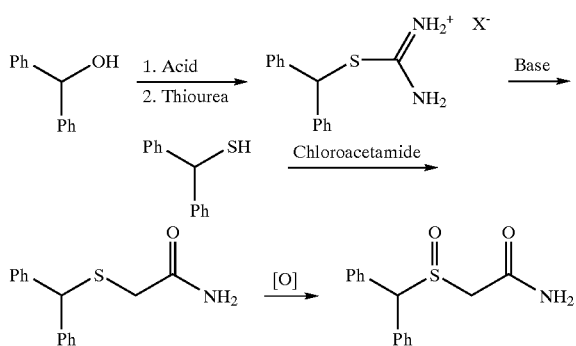

Scheme 1

In Step 1, the alcohol group of the benzhydrol is converted into a readily cleavable leaving group, preferably by addition of an acid. The resultant compound is reacted with thiourea to form the corresponding S-benzhydrylthiouronium salt, wherein the $X^-$ is the counterion from the corresponding acid.

In one embodiment, the benzhydrol is combined with an suitable amount of thiourea and an suitable acid in a suitable solvent. The benzhydrol can be combined with the thiourea, followed by addition of the acid, or the thiourea can be combined with the acid, followed by addition of the benzhydrol. It is desirable to add at least one equivalent of acid to allow the reaction to go to completion. The amount of acid can be from about 1 to 10 equivalents, with about 1–3 equivalents being preferred, and about 1.2 equivalents being more preferred. Similarly, it is desirable to add at least one equivalent of the thiourea to allow the reaction to go to completion. The amount of thiourea can be from about 1 to 10 equivalents, with about 1–3 equivalents being preferred, and about 1.2 equivalents being more preferred.

The suitable acids are those which allow conversion of the benzhydrol, in the presence of thiourea, to the S-benzhydrylthiouronium salt. Although a large group of acids are acceptable, mineral acids are preferred, including hydrobromic, hydrochloric and sulfuric acids, with hydrobromic acid being most preferred. Reaction of benzhydrol with hydrobromic acid yields the corresponding S-benzhydrylthiouronium bromide. Other preferable acids include organic acids, such as trifluoroacetic acid and benzene sulfonic acid.

Suitable solvent systems include water, and mixtures of water with organic solvents such as ethers, which include diethyl ether, tetrahydrofuran, 1,2-dimethoxyethane, and MTBE; polar organic solvents such as acetonitrile, methylene chloride, ethyl acetate, acetone; and aromatic solvents, such as benzene, toluene, ethylbenzene, xylene, chlorobenzene, orthodichlorobenzene; and hydrocarbon solvents such as hexane, heptane, methylchlorobenzene, and methylcyclohexane. Preferred solvents include water/tetrahydrofuran mixtures, water/chlorobenzene mixtures and water/MTBE mixtures.

The reaction temperature can range from room temperature to the reflux of the solvent system. Preferably, the reaction mixture is warmed, from about 60–70° C.

The reaction time is one that results in a maximal conversion of the starting materials to the desired product, and can range from about 1–24 h, preferably from about 1–5 h, and more preferably for about 3 h. The reaction can be monitored by standard methodologies, such as by TLC, HPLC and $^1$H NMR analyses. The reaction is considered complete when the analysis indicates a maximum amount of the desired product in comparison to the starting materials and by-products.

For example, in Step 1, benzhydrol can be combined with thiourea and about 48% HBr, and the reaction mixture is heated to about 60–70° C. and stirred until the reaction is complete. The reaction mixture can be directly used in the next step without work-up or purification, or the reaction mixture can be cooled to room temperature or placed on an ice bath to precipitate S-benzhydrylthiouronium bromide, which can be filtered and washed and purified, if desired, for the next step.

In Steps 2 and 3, the S-benzhydrylthiouronium bromide formed in step 1 is converted to the corresponding thiol, and then reacted with chloroacetamide to form 2-(benzhydrylthiol) acetamide. For example, the thiourea can be converted to the thiol by reaction with a suitable base. The reaction steps 2 and 3 can be carried out in the same reaction vessel as was employed in step 1, without isolation of any intermediates.

Suitable bases are those that convert the S-benzhydrylthiouronium salt to the corresponding benzhydrylthiol, such as sodium, lithium and potassium hydroxides and alkoxides, including tertiary alkoxides, such as tert-butoxide. Other suitable bases include sodium, lithium and potassium salts of carbonates. Preferred bases are sodium and potassium hydroxide. The reaction temperature for either step can range from room temperature to the reflux temperature of the solvent system. Preferably, the reaction mixture is warmed, from about 60–70° C. The solvent system can be the same one used in the previous step, or may additionally include a suitable organic solvent, for example, a polar protic solvent, such as an alcohol, an aromatic solvent or an ether solvent. Alcohols can include methanol, ethanol, isopropanol, cyclohexanol; aromatic solvents can include benzene, toluene, chlorobenzene; and ethers can include tetrahydrofuran, 1,2-dimethoxyethane and MTBE.

For example, the thiourea can be treated with an aqueous base, preferably NaOH or KOH. The reaction mixture is stirred, typically at room temperature, until the reaction is complete. The reaction mixture is typically warmed (typically about 70–80° C.), and chloroacetamide is added. The chloroacetamide can be added as either a powder, or an aqueous, organic, or partially aqueous solution, with an additional organic solvent, such as tetrahydrofuran. It is desirable to add at least one equivalent of chloroacetamide to allow the reaction to go to completion. The amount of chloroacetamide can be from about 1 to 10 equivalents, with a slight excess (about 1.05–2.0 mol excess) being preferred, and about 1.2 equivalents being more preferred. The reaction mixture is then stirred at the elevated temperature (typically about 70–80° C., although in some cases, up to about 100–110° C.) for an appropriate amount of time until the reaction is complete. The reaction mixture can then be cooled, and additional water may be added, and the aqueous layer is separated from the organic layer. The water layer can then be washed with an suitable organic solvent, and the organic extractions can be combined with the organic layer. The organic portion can be worked up and a crude product isolated for use in the next step, or it can be directly used in the next step.

In Step 4, the 2-(benzhydrylthiol) acetamide is oxidized with an suitable oxidizing agent in an suitable solvent to generate modafinil. A suitable oxidizing agent is one which oxidizes the sulfide group of the 2-(benzhydrylthiol) acetamide to the sulfoxide, with minimal overoxidation to the sulfone. The oxidation step can be carried out in the same reaction vessel as was employed in the previous steps. The corresponding product can be isolated and purified by methods well-known in the art.

Suitable oxidizing agents can include m-CPBA; sodium periodate; or hydrogen peroxide, benzoyl peroxide, t-butylhydroperoxide, wherein each peroxide is optionally in combination with a suitable acid. A suitable acid includes carboxylic acids, such as acetic acid, trifluoroacetic acid, benzoic acid, or n-butyric acid; aqueous solutions of an inorganic acid, such hydrochloric, hydrobromic or sulfuric acid; or an appropriate Lewis acid. For example, in step 4, acetic acid can be added to the reaction vessel, followed by slow addition of hydrogen peroxide. The amount of acetic acid can be from about 1 to 10 equivalents, with about 2–5 equivalents being preferred, and about 2.5–3.5 equivalents being more preferred. It is desirable to add at least one equivalent of hydrogen peroxide to allow oxidation of the sulfide group in 2-(benzhydrylthiol) acetamide to the corresponding sulfoxide. The amount of hydrogen peroxide can be added with a slight excess (from about 1.2 to 2 equivalents), with care taken not to allow overoxidation of the sulfoxide to the corresponding sulfone. Additional solvents can optionally be added to the reaction mixture if additional solubilization of the reagents is desired. Such solvents include tetrahydrofuran, methanol or acetone. The reaction temperature can range from room temperature to the reflux of the solvent system. Preferably, the reaction mixture is run at room temperature, or with slight warming to about 50–60° C. Following addition of the hydrogen peroxide, the reaction mixture is stirred until the desired amount of oxidation is obtained. The reaction mixture can be cooled, and may also be quenched by the addition of a quenching agent, such as bisulfite. Alternatively, m-CPBA can be slowly added to a cooled solution of 2-(benzhydrylthiol) acetamide (preferably about −15° C. to −25° C.). The reaction mixture can be stirred at the cool temperature until the reaction is complete, and worked up by conventional techniques.

The product can be isolated by methods well-known in the art, such as by precipitation, or by extraction. The product can be purified by means well-known in the art, such as by recrystallization or chromatography. Typical recrystallization solvents include methanol, and methanol/water solutions.

It is recognized that the product of the present invention, modafinil, may exist in enantiomeric forms. It is recognized that enantiomers of pharmaceutical agents may have different biological and pharmacological activity based on the particular configuration of the atoms involved, and that one enantiomer may be more useful in treating a medicinal indication over the other, and conversely. Accordingly, although modafinil is normally prepared as a racemate and can conveniently be used as such, individual enantiomers, (R)-modafinil and (S)-modafinil, can be isolated by conventional techniques if so desired. The racemate of modafinil, individual R- and S-enantiomers and mixtures thereof form part of the present invention.

It is well known in the art how to isolate optically active enantiomers. The specific enantiomers of modafinil can be resolved from a racemic mixture and recovered by techniques known in the art, such as resolution of racemic forms, normal, reverse-phase, and chiral chromatography. Direct separation of enantiomers by chromatography, especially liquid chromatography, is widely used. Industrial methods for the preparation of pure enantiomers constitute the resolution of racemates by methods such as: direct preferential crystallization, crystallization of the distereomeric salts, kinetic resolution, enzymatic resolution, and differential absorption. For example, two enantiomers may be separated by diastereomer crystallization, which generally involves reaction of the racemate with an optically pure acid or base (the resolving agent) to form a mixture of diastereomeric salts, which subsequently are separated by crystallization. Diastereomeric crystallization is widely used on industrial scale using a resolving agent, for example, camphor sulphonic acid, tartaric acid, maleic acid, mandelic acid, phenoxy propionic acid, hydratopic acid, brucine, quinine, ephedrine, .alpha.-methylbenzylamine, amphetamine, deoxyehedrine, and N-methyl D-glucamine, etc. Once separated by, for example, fractional crystallization, or more commonly, chromatography, the diastereomers are re-converted back into the corresponding enantiomers, which are now optically pure. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

EXAMPLES

The following examples are meant to be illustrative of the present invention. These examples are presented to exemplify the invention, and are not intended, nor are they to be construed, to limit the scope of the invention.

Example 1

To a suspension of benzhydrol (35.00 g, 0.188 mol, 1 equivalent) and thiourea (17.40 g, 0.226 mol, 1.20 equivalents) in tetrahydrofuran/water (35.5 ml/52.5 ml), was added an aqueous 48% HBr solution (25.3 ml, 0.226 mol, 1.2 equivalents) over a 10 min period. During the addition, the reaction mixture is heated to 70° C. After 3 h stirring at 70° C., the uronium intermediate was hydrolyzed by addition of an aqueous 9.3N potassium hydroxide solution (58 ml, 0.542 mol, 2.88 equivalents) over a 55 min period. After 1.5 h stirring at 70° C., chloroacetamide (26.6 g, 0.282 mol, 1.5 equivalents) in a tetrahydrofuran/water (80 ml/79 ml) solution was added over 15 min. After 1 h stirring at 70° C., the reaction mixture was cooled down to 55° C. and the stirring was stopped. The lower aqueous phase was removed, and the reaction mixture was again stirred. Acetic acid (34.7 ml, 0.601 mol, 3.2 equivalents) was added.

Hydrogen peroxide 30% (38.4 ml, 0.376 mol, 2 equivalents) was slowly added over 30 min. After 1 h stirring, the reaction mixture was cooled to 20° C. and water (263 ml) was added. The resultant suspension was stirred at 0° C. overnight. The suspension was then filtered and the solid was washed with water, and dried to yield modafinil (47.9 g, 80.4%). The crude modafinil was purified by recrystallization in methanol.

Example 2

A suspension of benzhydrol (200.00 g, 1.075 mol, 1 equivalent) and thiourea (99.4 g, 1.293 mol, 1.20 equivalents) in monochlorobenzene/water (477 ml/300.5 ml) was heated at 70° C. An aqueous 48% HBr solution (145 ml, 1.29 mol, 1.2 equivalents) was then added over a 5 min period. After 3 h stirring at 70° C., the uronium intermediate was hydrolyzed by addition of an aqueous 9.3N potassium hydroxide solution (321.7 ml, 2.825 mol, 2.63 equivalents) over a 50 min period. After 1.5 h stirring at 70° C., chloroacetamide (152.3 g, 1.612 mol, 1.5 equivalents) in powder form was added for over a 15 min period. After 30 min stirring at 70° C., the reaction mixture was cooled down to 55° C. and the stirring was stopped. The lower aqueous phase was removed, and water (600 ml) was added to the reactor. The reaction mixture was again stirred for 45 min. The lower aqueous phase was then removed. Acetic acid (173.3 ml, 3.000 mol, 2.79 equivalents) was added. Hydrogen peroxide 30% (175.4 ml, 1.718 mol, 1.6 equivalents) was slowly added for 80 min. After 50 minutes of stirring at 55° C., the reaction mixture was quenched with an aqueous sodium bisulfite solution (275 g). The lower aqueous phase was removed and the reaction mixture was cooled 0–5° C. Monochlorobenzene (386 g) was added to dilute the reaction mixture. The resultant suspension was then filtered, and the solid was washed with water and monochlorobenzene, and dried to yield modafinil (216.7 g, global yield 69.3%, strength 93.9 wt. %). The crude modafinil was purified by recrystallization in methanol.

As those skilled in the art will appreciate, numerous changes and modifications may be made to the embodiments of the invention without departing from the spirit of the invention. It is intended that all such variations fall within the scope of the invention.

What is claimed is:

1. A process of preparing modafinil comprising the step of reacting chloroacetamide with benzhydrylthiol to form 2-(benzhydrylthiol) acetamide.

2. A process of preparing modafinil comprising the steps of reacting chloroacetamide with benzhydrylthiol to form 2-(benzhydrylthiol) acetamide, and oxidizing 2-(benzhydrylthiol) acetamide.

3. The process of claim 1, wherein the benzhydrylthiol is formed by reacting benzhydrol with thiourea and a suitable acid to form a S-benzhydrylthiouronium salt, followed by reacting the S-benzhydrylthiouronium salt with a suitable base.

4. The process of claim 3, wherein the steps are conducted in the same reaction vessel without isolation of any intermediates.

5. The process of claim 3, wherein the suitable base is a metal hydroxide.

6. The process of claim 5, wherein the metal hydroxide is sodium hydroxide or potassium hydroxide.

7. The process of claim 3, wherein the suitable acid is hydrobromic acid, hydrochloric or sulfuric acid.

8. The process of claim 3, wherein the reactions are conducted in a solvent system comprising water and an organic solvent selected from tetrahydrofuran, 1,2-dimethoxyethane, MTBE, acetonitrile, chlorobenzene, ortho-dichlorobenzene, or methylcyclohexane.

9. The process of claim 8, wherein the temperature is from about 25° C. to the refluxing temperature of the solvent system.

10. The process of claim 9, wherein the temperature is from about 25–75° C.

11. A process of preparing modafinil, comprising:
(1) reacting benzhydrol with a suitable acid and thiourea to form a S-benzhydrylthiouronium salt;
(2) reacting the S-benzhydrylthiouronium salt with a suitable base to form benzhydrylthiol;
(3) reacting the benzhydrylthiol with chloroacetamide to form 2-(benzhydrylthiol) acetamide;
(4) oxidizing 2-(benzhydrylthiol) acetamide with a suitable oxidizing agent to form modafinil.

12. The process of claim 11, wherein the suitable acid is selected from either hydrobromic or hydrochloric acid; and the suitable base is selected from potassium hydroxide or sodium hydroxide; and the process steps are conducted using either a water/tetrahydrofuran or a water/chlorobenzene solvent system.

13. The process of claim 11, wherein:
(1) an aqueous 48% hydrobromic acid solution (about 1–10 equivalents) is added to benzhydrol and thiourea (about 1–10 equivalents) at a temperature of about 25–75° C., to form S-benzhydrylthiouronium salt;
(2) an aqueous solution of potassium hydroxide (about 1–10 equivalents) is added, at a temperature of about 25–75° C., to the S-benzhydrylthiouronium salt to form the benzhydrylthiol;
(3) chloroacetamide as either a powder, or in solution with either water or a water/tetrahydrofuran mixture (about 1–10 equivalents) is combined with the benzhydrylthiol at a temperature of about 25–75° C. to form 2-(benzhydrylthiol) acetamide.

14. The process of claim 11, wherein the temperature for steps 1, 2, and 3 is from about 50–75° C.

15. The process of claim 11, wherein the 2-(benzhydrylthiol) acetamide is oxidized with an oxidizing agent selected from m-chloroperoxybenzoic acid, sodium periodate, or hydrogen peroxide wherein the hydrogen peroxide may optionally be combined with an acid selected from hydrochloric or acetic acid.

16. The process of claim 15, wherein a 30% solution of hydrogen peroxide (about 1–2 equivalents) is combined with 2-(benzhydrylthiol) acetamide and acetic acid at a temperature of about 25–75° C.

17. The process of claim 16, wherein the preparation of modafinil is conducted in the same reaction chamber without isolation of any intermediates.

18. A process of preparing modafinil comprising:
(1) reacting benzhydrol, thiourea (about 1–3 equivalents) and an aqueous 48% HBr solution (about 1–3 equivalents) in aqueous tetrahydrofuran at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in an aqueous tetrahydrofuran solution, with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil.

19. A process of preparing modafinil comprising:
(1) reacting benzhydrol, thiourea (about 1–3 equivalents) and an aqueous 48% HBr solution (about 1–3 equivalents) in aqueous chlorobenzene at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in powder form with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil.

20. The process of claim 2 further comprising the steps of reacting chloroacetamide with benzhydrylthiol to form 2-(benzhydrylthiol) acetamide, oxidizing 2-(benzhydrylthiol) acetamide to form modafinil, and isolating (R)-modafinil from modafinil.

21. The process of claim 11 further comprising:
(1) reacting benzhydrol with a suitable acid and thiourea to form a S-benzhydrylthiouronium salt;
(2) reacting the S-benzhydrylthiouronium salt with a suitable base to form benzhydrylthiol;
(3) reacting the benzhydrylthiol with chloroacetamide to form 2-(benzhydrylthiol) acetamide;
(4) oxidizing 2-(benzhydrylthiol) acetamide with a suitable oxidizing agent to form modafinil; and
(5) isolating (R)-modafinil from modafinil.

22. The process of preparing of claim 18 further comprising:
(1) reacting benzhydrol, thiourea (about 1–3 equivalents) and an aqueous 48% HBr solution (about 1–3 equivalents) in aqueous tetrahydrofuran at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in an aqueous tetrahydrofuran solution, with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil; and
(5) isolating (R)-modafinil from modafinil.

23. The process of claim 19 further comprising:
(1) reacting benzhydrol, thiourea (about 1–3 equivalents) and an aqueous 48% HBr solution (about 1–3 equivalents) in aqueous chlorobenzene at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in powder form with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil; and
(5) isolating (R)-modafinil from modafinil.

24. The process of claim 2 further comprising the steps of reacting chloroacetamide with benzhydrylthiol to form 2-(benzhydrylthiol) acetamide, oxidizing 2-(benzhydrylthiol) acetamide to form modafinil, and isolating (S)-modafinil from modafinil.

25. The process of claim 11 further comprising:
(1) reacting benzhydrol with a suitable acid and thiourea to form a S-benzhydrylthiouronium salt;
(2) reacting the S-benzhydrylthiouronium salt with a suitable base to form benzhydrylthiol;
(3) reacting the benzhydrylthiol with chloroacetamide to form 2-(benzhydrylthiol) acetamide;
(4) oxidizing 2-(benzhydrylthiol) acetamide with a suitable oxidizing agent to form modafinil; and
(5) isolating (S)-modafinil from modafinil.

26. The process of preparing of claim 18 further comprising:
(1) reacting benzhydrol, thiourea (about 1–3 equivalents) and an aqueous 48% HBr solution (about 1–3 equivalents) in aqueous tetrahydrofuran at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in an aqueous tetrahydrofuran solution, with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil; and
(5) isolating (S)-modafinil from modafinil.

27. The process of claim 19 further comprising:
(1) reacting benzhydrol, thiourea (about 1–3 equivalents) and an aqueous 48% HBr solution (about 1–3 equivalents) in aqueous chlorobenzene at about 70° C. to form S-benzhydrylthiouronium salt;
(2) reacting the S-benzhydrylthiouronium salt with an aqueous potassium hydroxide solution (about 2–5 equivalents) at about 70° C. to form benzhydrylthiol;
(3) reacting chloroacetamide (about 1.05–2 equivalents) in powder form with the benzhydrylthiol at about 70° C., to form 2-(benzhydrylthiol) acetamide;
(4) reacting the 2-(benzhydrylthiol) acetamide with acetic acid (about 2–5 equivalents) and a 30% aqueous hydrogen peroxide solution (about 1.2–2 equivalents) to form modafinil; and
(5) isolating (S)-modafinil from modafinil.

* * * * *